(12) United States Patent
Minamiura et al.

(10) Patent No.: US 7,414,244 B2
(45) Date of Patent: Aug. 19, 2008

(54) MIXING RATION DETECTING APPARATUS, METHOD OF CONTROLLING MIXING RATION DETECTING APPARATUS, AND FUEL CELL SYSTEM INCORPORATING MIXING RATIO DETECTING APPARATUS

(75) Inventors: Takeshi Minamiura, Gunma (JP); Takashi Yasuo, Ashikaga (JP); Ryoko Kubo, Gunma (JP)

(73) Assignee: Sanyo Electric Co., Ltd., Osaka (JP)

( * ) Notice: Subject to any disclaimer, the term of this patent is extended or adjusted under 35 U.S.C. 154(b) by 0 days.

(21) Appl. No.: 11/169,711

(22) Filed: Jun. 30, 2005

(65) Prior Publication Data

US 2006/0000975 A1     Jan. 5, 2006

(30) Foreign Application Priority Data

Jun. 30, 2004    (JP) ............................. 2004-194260

(51) Int. Cl.
*G01J 5/02*     (2006.01)
*G01J 5/00*     (2006.01)
*G01V 5/08*     (2006.01)
*H01M 2/00*     (2006.01)

(52) U.S. Cl. .............................. 250/339.12; 250/341.8; 250/341.1; 250/343; 250/338.1; 429/34

(58) Field of Classification Search ................... 429/12, 429/34; 250/341.8, 341.1, 339.12
See application file for complete search history.

(56) References Cited

U.S. PATENT DOCUMENTS 5,096,277 A * 3/1992 Kleinerman ................. 385/12

FOREIGN PATENT DOCUMENTS

| JP | 04-200071 | 7/1992 |
|---|---|---|
| JP | 10-019766 | 1/1998 |
| JP | 11-037936 | 2/1999 |
| JP | 11-78686 | 2/1999 |
| JP | 2001-124695 | 5/2001 |
| KR | 10-2003-0002047 | 1/2003 |
| KR | 10-2004-0033405 | 4/2004 |
| KR | 10-2004-0043436 | 5/2004 |
| WO | WO 90/12890 | 11/1990 |

OTHER PUBLICATIONS

The Random House College Dictionary, 1980, Revised Edition, Section O.*

(Continued)

*Primary Examiner*—Raymond Alejandro
*Assistant Examiner*—Helen O. Chu
(74) *Attorney, Agent, or Firm*—McDermott Will & Emery LLP (57) ABSTRACT

A mixture ratio detecting apparatus comprises: a light source which emits light including light of an infrared region; a first light detecting unit which detects the light of the infrared region from the light source; a second light detecting unit which detects light of a region having a range different from that of the first light detecting unit; and a control unit which outputs a signal pertaining to a mixture ratio based on signals from the first light detecting unit and the second light detecting unit, and controls the light source, the first light detecting unit, and the second light detecting unit.

12 Claims, 9 Drawing Sheets

OTHER PUBLICATIONS

Korean Office Action, with English Translation, issued in corresponding Korean Patent Application KR 10-2005-40937 dated on Jan. 11, 2007.

Japanese Office Action, with English Translation, issued in corresponding Japanese Patent Application No. 2004-194260, dated on Feb. 27, 2007.

* cited by examiner

CROSS SECTION A

MIXING RATION DETECTING APPARATUS, METHOD OF CONTROLLING MIXING RATION DETECTING APPARATUS, AND FUEL CELL SYSTEM INCORPORATING MIXING RATIO DETECTING APPARATUS

BACKGROUND OF THE INVENTION

1. Field of the Invention

The invention relates to a mixing ratio detecting apparatus for detecting the mixing ratio of a component to be detected to a mixture solution containing the component to be detected. In particular, the invention relates to a mixing ratio detecting apparatus for detecting the mixing ratio of methanol and water to be used in a direct methanol fuel cell or the like. In other words, the invention relates to a so-called methanol aqueous solution concentration sensor.

2. Description of the Related Art

Fuel cells are devices for generating electric energy from hydrogen and oxygen, and are capable of providing high generation efficiency. The fuel cells chiefly has the following characteristics: high generation efficiency is expected even in smaller scales because of the direct generation mode without thermal- or kinetic-energy processes as in conventional generation modes; and excellent environmental friendliness is obtained from low emission of nitrogen compounds as well as reduced noise and vibrations. Since the fuel cells can thus use the chemical energy of the fuel effectively and have the environment-friendly characteristics, they are expected as energy supply systems to bear the 21st century. For various applications ranging from large-scale power generation to small-scale generation, such as space technologies, automobiles, and portable devices, the fuel cells are attracting attention as promising novel generation systems. Technological development toward practical use has thus been made in earnest.

Above all, solid polymer type fuel cells are characterized in lower operating temperatures and higher output densities as compared to the other types of fuel cells. Among various forms of solid polymer type fuel cells, a direct methanol fuel cell (DMFC) has recently been gaining attention in particular. The DMFC is one in which a methanol aqueous solution, the fuel, is supplied directly to the anode without any modification so that electricity is generated through the electrochemical reaction between the methanol aqueous solution and oxygen. In this electrochemical reaction, carbon dioxide and generated water are emitted from the anode and the cathode as reaction products, respectively. As compared to hydrogen, the methanol aqueous solution provides higher energy per unit volume, is well-suited to storage, and has low risk of explosion or the like. Applications such as the power sources of automobiles and cellular phones are thus expected.

When the methanol aqueous solution to be supplied to the anode of the DMFC is too high in concentration, there can occur the problem that degradation of the solid polymer film inside the DMFC is promoted with a drop in reliability. When the concentration is too low, it is impossible to obtain a sufficient output from the DMFC. The concentration is thus preferably adjusted within the range of 0.5 and 4 mol/L, and desirably 0.8 and 1.5 mol/L. It has been found that the range of concentrations can be narrowed to stabilize the operation of the DMFC.

Now, take the case of a system having a DMFC. For the sake of operating the DMFC for a long period and reducing the size and weight of the system as well, the system is typically provided with a tank for containing methanol having a high concentration of 20 mol/L or above. Here, the methanol must be thinned and adjusted in concentration before supplied to the anode of the DMFC. Then, a methanol aqueous solution concentration sensor of high precision and small size has been sought after in order to adjust the methanol aqueous solution to a concentration of 0.8 to 1.5 mol/L inside the system. Researches have been made various types of sensors including optical type (see Japanese Patent Laid-Open Publication No. 2001-124695), supersonic type, and specific gravity type. Nevertheless, the methanol aqueous solution concentration sensor to be implemented on a DMFC system is yet to be developed since it requires high precision, small size, light weight, low cost, and low power consumption.

The foregoing optical type concentration sensors have had the possibility of a drop in measurement precision if the aqueous solution contains air bubbles, contaminations, etc. Besides, full-time operation of the detecting apparatus has produced the problem of large power consumption for measurement.

SUMMARY OF THE INVENTION

The present invention has been achieved in view of the foregoing problems. It is thus an object of the present invention to provide a concentration sensor of high precision, small size, light weight, low cost, and low power consumption, and more particularly to provide a methanol aqueous solution concentration sensor to be implemented on a DMFC.

To achieve the foregoing object, the present invention provides a mixing ratio detecting apparatus for detecting a mixing ratio of a component to be detected to a mixture solution containing the component to be detected. The apparatus comprises: a light source which emits light including at least light of an infrared region; an infrared light detecting unit which detects the light of the infrared region, the infrared light detecting unit being arranged in a position capable of receiving the light of the infrared region from the light source through the mixture solution; and a control unit which outputs a signal pertaining to the mixing ratio based on a signal from the infrared light detecting unit, and controls the light source and the infrared light detecting unit.

Specifically, the mixing ratio detecting apparatus is one for detecting a mixing ratio of an alcohol to a mixture solution containing the alcohol, the apparatus comprising: a light source which emits light including at least light of an infrared region; a first light detecting unit which detects the light of the infrared region, the first light detecting unit being arranged in a position capable of receiving the light of the infrared region from the light source through the mixture solution; a second light detecting unit which detects light of a region having a range different from that of the first light detecting unit, the second light detecting unit being arranged in a position capable of receiving the light from the light source through the mixture solution; and a control unit which outputs a signal pertaining to the mixing ratio based on signals from the first light detecting unit and the second light detecting unit, and controls the light source, the first light detecting unit, and the second light detecting unit.

According to the foregoing configuration, the apparatus can be reduced in size and weight while achieving detection with high precision.

The second light detecting unit may be a visible light detecting unit which detects light of a visible light region. Here, the visible light detecting unit is arranged in a position capable of receiving the light of the visible light region from the light source through the mixture solution.

This makes it easier to detect the effect of air bubbles, contaminations, etc.

An incandescent lamp may be used as the light source, whereby the apparatus can be fabricated at low cost.

The first light detecting unit may comprise a photoreceptor capable of detecting the light of the visible light region and the light of the infrared region, and an infrared light transmission unit which transmits the light of the infrared region. The second light detecting unit may comprise a photoreceptor capable of detecting the light of the visible light region and the light of the infrared region, and a visible light transmission unit which transmits the light of the visible light region. Alternatively, a diffraction unit which diffracts the light from the light source at different angles depending on wavelengths may be arranged on an optical path leading from the light source to the first light detecting unit and the second light detecting unit. Here, the first light detecting unit is arranged in a position capable of receiving the light of the infrared region diffracted by the diffraction unit. The second light detecting unit is arranged in a position capable of receiving the light of the visible light region diffracted by the diffraction unit.

This can reduce the types of the parts, allowing cost reduction.

A reflection unit which reflects the light from the light source may be arranged on an optical path leading from the light source to the first light detecting unit and the second light detecting unit. The first light detecting unit and the second light detecting unit are arranged in positions capable of receiving the light reflected by the reflection unit.

Specifically, the first light detecting unit and the second light detecting unit are arranged in positions such that the light source, the first light detecting unit, and the second light detecting unit are opposed to the reflection unit across the mixture solution.

This facilitates the layout of the wiring from the control unit.

A light shield unit which shields light incident on the first light detecting unit and the second light detecting unit directly from the light source without the medium of the reflection unit may be arranged between the light source and the first and second light detecting units.

This allows more accurate detection.

The first light detecting unit may be arranged farther from the light source than the second light detecting unit is. Alternatively, a temperature detecting unit which detects a temperature of the mixing ratio detecting apparatus may be provided. Here, the control unit makes a temperature correction to the signals obtained from the first light detecting unit and the second light detecting unit by using the temperature detected by the temperature detecting unit.

Consequently, the infrared detecting unit susceptible to heat rays can conduct more accurate detection.

At least one major surface of the mixing ratio detecting apparatus may be covered with a heat insulating member.

Consequently, even when air bubbles adhere to the optical path, it is easy to remove the air bubbles by the heat from the light source.

The present invention also provides a method of controlling a mixing ratio detecting apparatus, the method comprising turning on the light source, and turning off the light source. The turning-on and the turning-off are repeated at predetermined intervals.

This makes it possible to reduce the power consumption necessary for detection.

When an abnormal signal is detected from the first light detecting unit or the second light detecting unit, the repetition of the turning-on and the turning-off at the predetermined intervals may be stopped to keep the light source on for a predetermined period.

Consequently, even when air bubbles adhere to the optical path, it is possible to remove the air bubbles by the heat from the light source.

The method may comprises at least: applying a first voltage intermediate between when turning on and turning off the light source to the light source; and applying a second voltage necessary for turning on the light source to the light source. Here, the applying of the first voltage, the applying of the second voltage, and the turning-off are repeated at predetermined intervals.

This allows more accurate detection.

The present invention also provides a fuel cell system comprising a fuel cell body having an anode for a liquid fuel to be supplied to, the system implementing a mixing ratio detecting apparatus for detecting a mixing ratio of a fuel component to the liquid supplied to the fuel cell body. The system comprises: a high concentration fuel unit which stores a fuel having a concentration higher than that of the liquid fuel to be supplied to the fuel cell body; a liquid fuel supply unit which dilutes the high concentration fuel to supply the liquid fuel to the fuel cell body; and a system control unit which controls the fuel cell system. The system control unit issues an instruction to supply the high concentration fuel from the high concentration fuel unit to the liquid fuel supply unit in accordance with a signal from the mixing ratio detecting apparatus.

Consequently, the fuel cell system can be operated with stability.

The system control unit may issue an instruction to supply a predetermined amount of the high concentration fuel from the high concentration fuel unit to the liquid fuel supply unit when a signal indicating that the liquid fuel supplied to the fuel cell body falls to or below a predetermined concentration is transmitted from the mixing ratio detecting apparatus to the system control unit.

Consequently, the fuel cell system can be operated with stability without requiring volume control on a liquid fuel pump etc.

The mixing ratio detecting apparatus may be arranged in a liquid fuel supply pipe of the liquid fuel supply unit, the liquid fuel supply pipe lying in a stage before the liquid fuel is supplied to the fuel cell body.

This makes it possible to grasp the concentration of the fuel to be supplied to the fuel cell body with higher accuracy.

In the fuel cell system implementing any one of the mixing ratio detecting apparatuses described above, the system control unit may receive a signal pertaining to a flow rate of the liquid fuel from the liquid fuel supply unit. Here, the system control unit or the control unit of the mixing ratio detecting apparatus makes a flow rate correction to the signals obtained from the first light detecting unit and the second light detecting unit by using the signal pertaining to the flow rate received by the system control unit.

This makes it possible to grasp the concentration of the fuel to be supplied to the fuel cell body with still higher accuracy, so that the fuel cell system can be operated with higher stability.

DETAILED DESCRIPTION OF THE INVENTION

Now, the configuration of a methanol aqueous solution concentration sensor (hereinafter, abbreviated as concentration sensor) 100 according to the present invention will be described in detail with reference to the drawings.

Figure 1A:
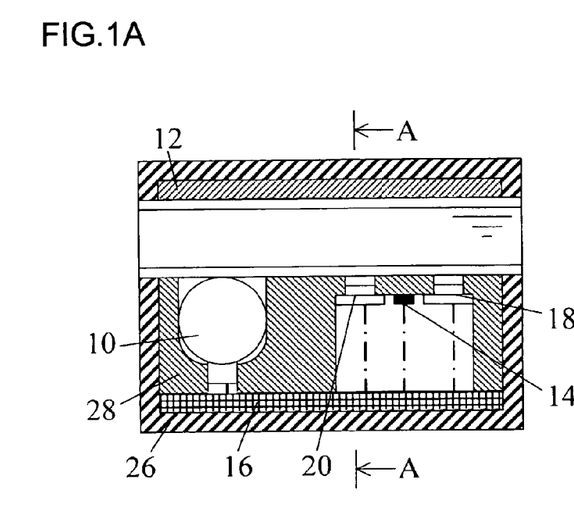
FIG. 1A is a schematic diagram showing the configuration of a concentration sensor according to an embodiment.
Figure 1B:
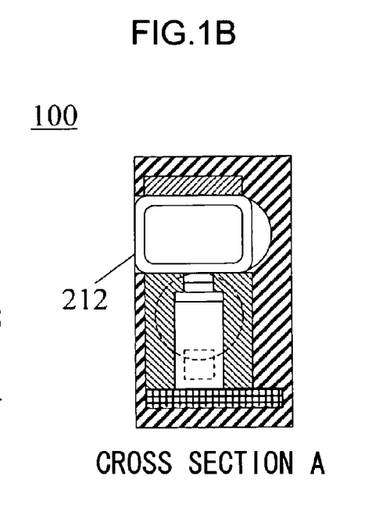
FIG. 1B is a sectional view taken along the plane A-A of FIG. 1A.
Figure 9:
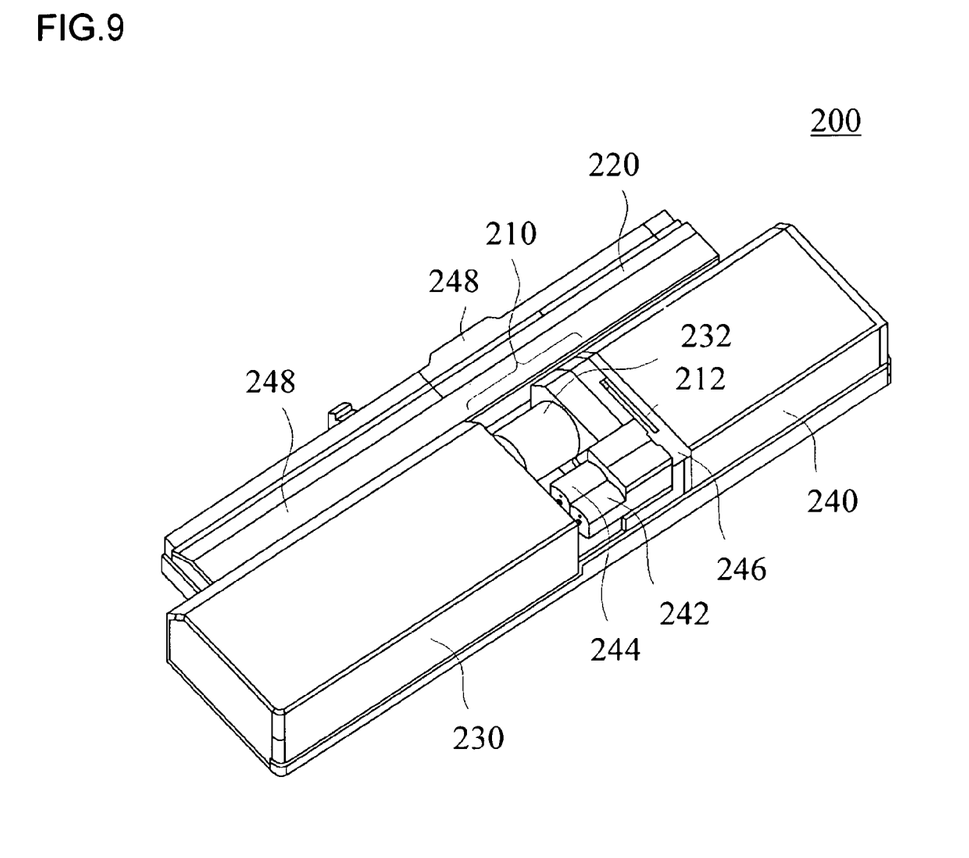
FIG. 9 is a block diagram showing the configuration of a DMFC system according to the embodiment.

FIG. 1A is a schematic diagram showing the configuration of the concentration sensor 100 according to the present embodiment. FIG. 1B is a sectional view taken along the plane A-A of FIG. 1A. The concentration sensor 100 is arranged in an S area of a DMFC system 200 shown in FIG. 9. More specifically, the concentration sensor 100 is arranged on a pipe 212 immediately before where a methanol aqueous solution is supplied to the anode of the DMFC. The methanol aqueous solution supply pipe 212 is unitized as shown in FIG. 9. A plurality of plate members made by injection molding a resin material are combined to constitute a piping unit 210.

The concentration sensor 100 comprises such components as a light source 10, one or a plurality of photoreceptors, a mirror 12, a thermistor 14, and a sensor control unit 16. The mirror 12 is opposed to the light source 10 and the photoreceptors across the methanol aqueous solution supply pipe 212. The thermistor 14 is arranged near the photoreceptors. The sensor control unit 16 exercises control on the light source 10, the photoreceptors, and the thermistor 14, and conducts signal transmission and reception. The present embodiment uses two photoreceptors 18 and 20. A first photoreceptor 18 has reception sensitivity to a near-infrared region around 1450 nm, which is the absorption wavelength of water. A second photoreceptor 20 has reception sensitivity to a visible light region, or wavelengths shorter than those of the first photoreceptor 18. The two types of photoreceptors can be used to measure the concentration of the methanol aqueous solution accurately. It is also possible to detect the presence of stains and contaminations from a combination of the signals of different wavebands.

The light source 10 is an incandescent lamp having a tungsten filament or the like. The incandescent lamp is suitable since it emits light ranging from the visible light region to the infrared region and is compact and inexpensive. In the present embodiment, an incandescent lamp rated at 100 mA and 5 V is used. For the mirror 12, one having high reflectance in the wide range from the visible light region to the near-infrared region is desirably selected. The thermistor 14 is interposed between the first photoreceptor 18 and the second photoreceptor 20, and is used to make a temperature correction to the signals from the photoreceptors 18 and 20. If it cannot be interposed, then the thermistor 14 is preferably arranged closer to the first photoreceptor 18 which is particularly susceptible to temperatures (heat rays).

The sensor control unit 16 comprises such components as a light source control circuit, an arithmetic circuit, and a communication circuit which are not shown. The light source control circuit includes a circuit which prevents a rush current from flowing immediately after the ON/OFF control of the light source 10, or immediately after a current is passed particularly when the light source 10 is an incandescent lamp as in the present embodiment. The rush current refers to the phenomenon that a current as high as 10 to 1000 times that in normal use flows because of low resistance of the cold filament, though for a period of the order of milliseconds. The arithmetic circuit calculates the concentration of the methanol aqueous solution based on the signals from the photoreceptors 18 and 20 and the signal from the thermistor 14. The communication circuit transmits the concentration of the methanol aqueous solution derived by the arithmetic circuit to exterior. These circuits may be arranged outside the concentration sensor 100 so that the external sensor control unit 16 calculates the concentration of the methanol aqueous solution based on the signals from the photoreceptors 18 and 20, the signal from the thermistor 14, etc.

Figure 2A:
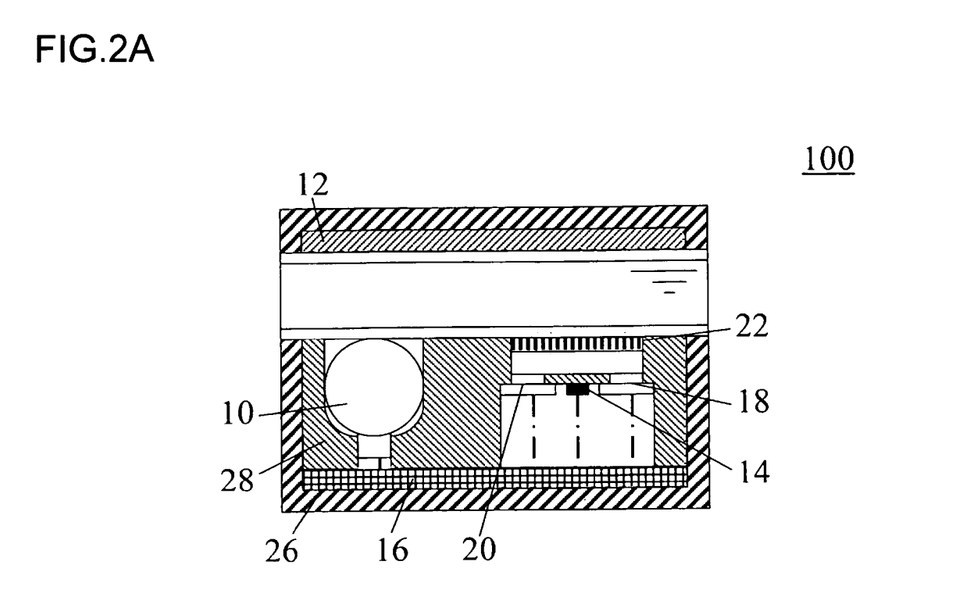
FIGS. 2A and 2B are schematic diagrams showing the configurations of concentration sensors according to other embodiments.
Figure 2B:
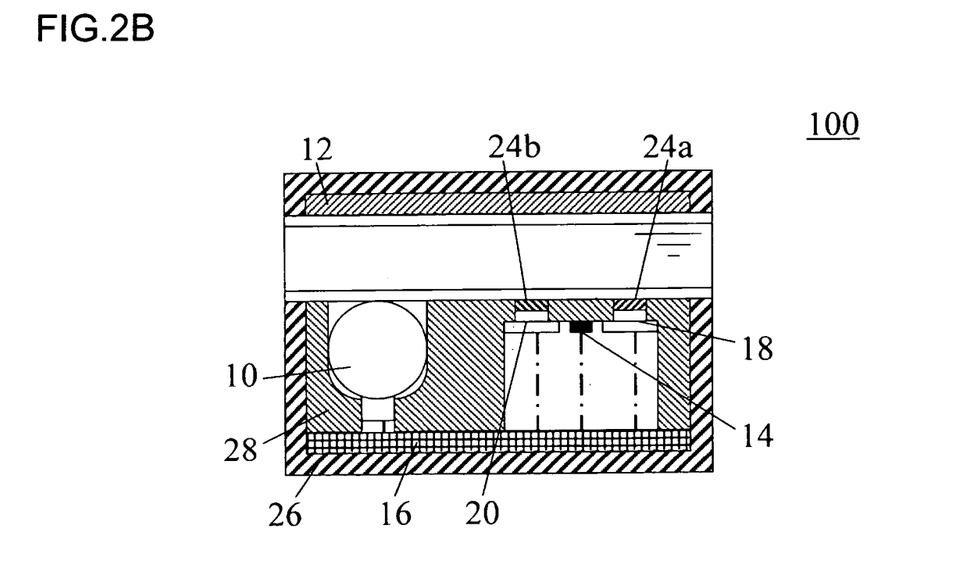

While the foregoing photoreceptors 18 and 20 have different sensitivity regions, the same effect can also be obtained by using devices having an identical sensitivity region as shown in FIGS. 2A and 2B. In FIG. 2A, a diffraction grating 22 is arranged in front of the photoreceptors 18 and 20. In FIG. 2B, a filter 24a for transmitting light of the near-infrared region and a filter 24b for transmitting light of the visible light region are arranged. In either case, the photoreceptor 18 for receiving the light of the near-infrared region is desirably arranged away from the light source 10 for the sake of reducing the susceptibility to the heat rays from the light source 10.

The concentration sensor 100 is covered with a heat insulator 26 so that the heat from the light source 10 will not be released to exterior but used to warm the methanol aqueous solution supply pipe 212. Moreover, the light source 10 can be placed near the methanol aqueous solution supply pipe 212 for more effective heating. Consequently, even if air bubbles adhere to the optical path of the concentration sensor 100 and block off the light to hinder concentration measurement, the heat from the light source 10 warms the air bubbles to expand and burst easily, or to grow in flow resistance and be carried away easily.

The light source 10 and the photoreceptors 18 and 20 are fitted and attached into a housing 28 which is made of a resin material. This attachment mode fixes the components in position, makes them less susceptible to disturbances such as an impact, and provides even a shielding effect. It becomes thus possible to block off the light which could reach from the light source 10 to the photoreceptors 18 and 20 directly without passing through the methanol aqueous solution.

Next, the method of controlling the concentration sensor 100 will be described in conjunction with Examples thereof.

EXAMPLE 1

Figure 3A:
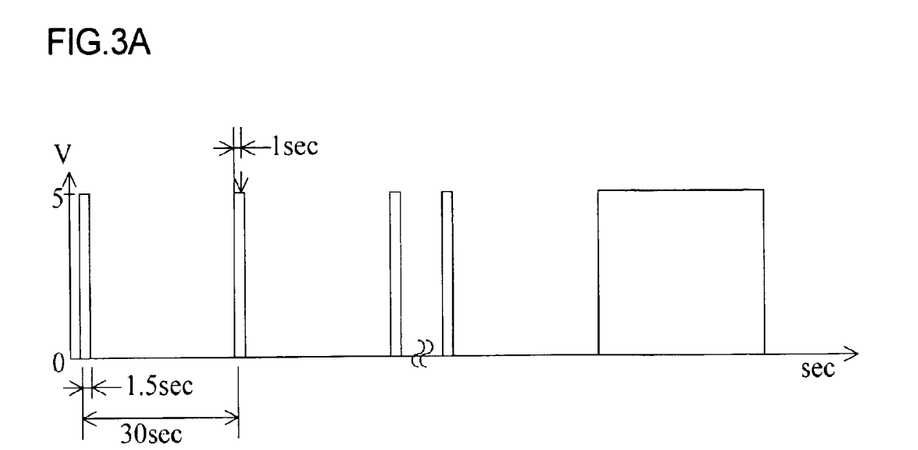
FIGS. 3A to 3C are graphs for showing the ON/OFF control of the light source and the measurements according to Example 1.

In Example 1, the light source 10 is lit for 1.5 sec at intervals of 30 sec as shown in FIG. 3A. When the light source 10 uses an incandescent lamp as in the embodiment, the rush current may affect as described above. In view of the settling time of the light from the light source 10, the photoreceptors 18 and 20 thus measure and convert the light into voltages after a lapse of 1 sec since the light source 10 is lit. Here, the photoreceptors 18 and 20 are previously set so that they output 5 V for the transmission light when the methanol aqueous solution has a predetermined high concentration of, for example, 2 mol/L.

Figure 3B:
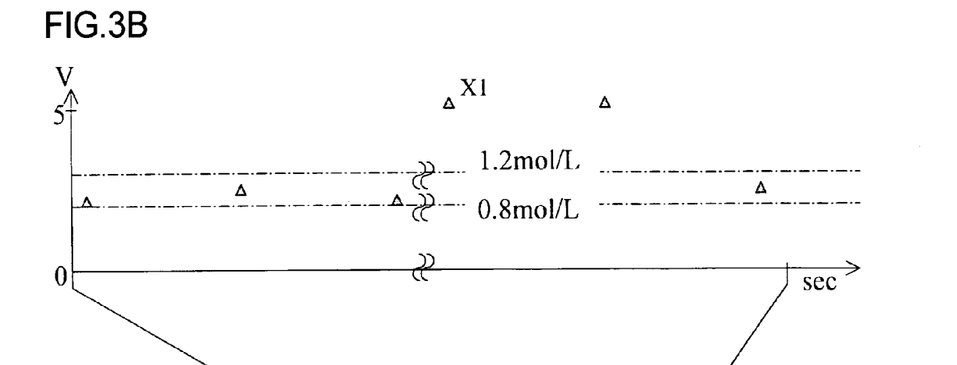
Figure 3C:
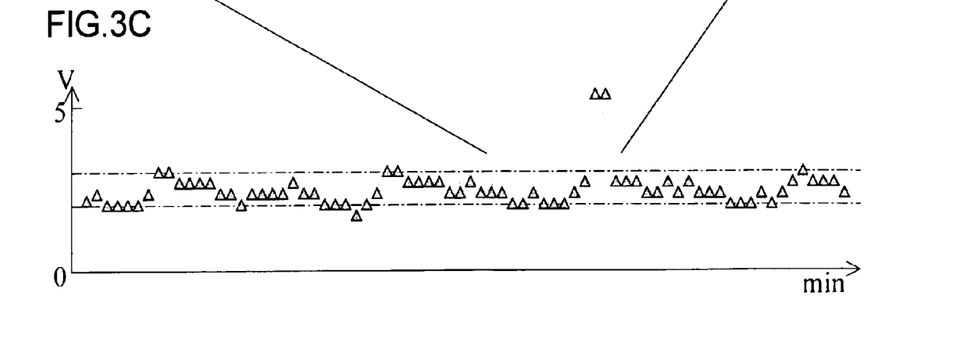

For normal operation, thresholds are set as shown in FIG. 3B, i.e., the upper limit is 1.2 mol/L and the lower limit is 0.8 mol/L, for example. When it is detected that the concentration falls below the lower limit for a predetermined period, a signal for informing of the low concentration is transmitted from the concentration sensor 10 to a control unit 220 of the DMFC system 200. In response, a high concentration of methanol is supplied from a high concentration methanol tank 230 to a buffer tank 232. Then, when the upper limit is exceeded or when a predetermined amount of methanol is supplied, the supply from the high concentration methanol tank 230 is stopped.

Figure 4A:
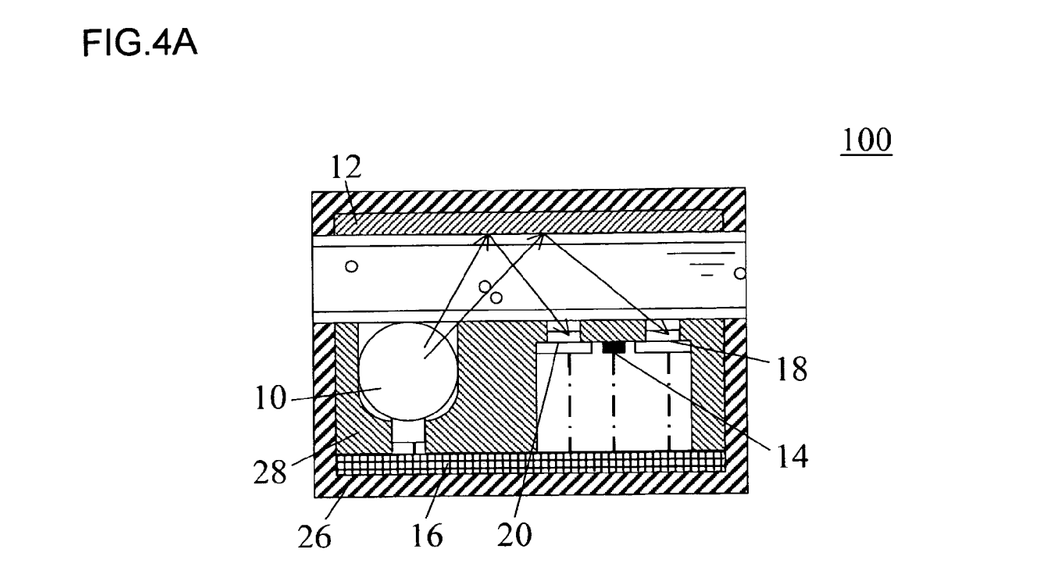
FIGS. 4A and 4B are schematic diagrams for situations where air bubbles get mixed in the methanol aqueous solution.
Figure 4B:
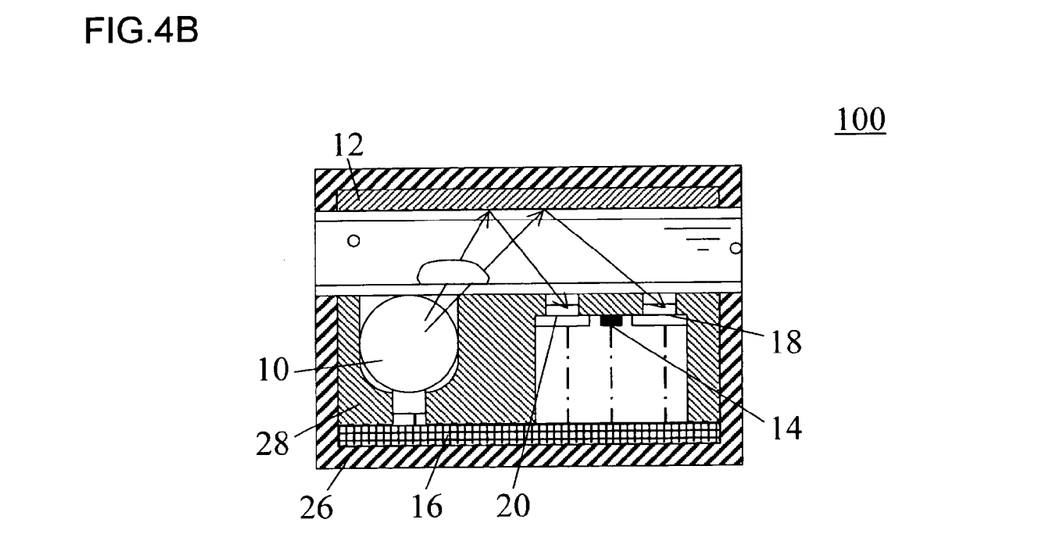

As shown in FIG. 4A, when air bubbles or the like get mixed in the methanol aqueous solution and come into the optical path during measurement, an abnormal value such as X1 in FIG. 3B is detected. If air bubbles or the like simply pass through during measurement, the value returns to normal at the next measurement. Nevertheless, if any bubble adheres to an interfering position on the optical path in the methanol aqueous solution supply pipe 212 as shown in FIG. 4B, the value will not return to normal by the next measurement. Then, another abnormal value is detected. In such cases, the light source 10 is not turned off in 1.5 sec but kept on so that the bubble expands due to the heat from the light source 10.

Such ON/OFF control on the light source 10 makes it possible to reduce the energy consumption of the light source 10. In addition, even when measurement is hindered by air bubbles or the like, it is possible to remove the air bubbles for proper measurement.

EXAMPLE 2

Figure 5:
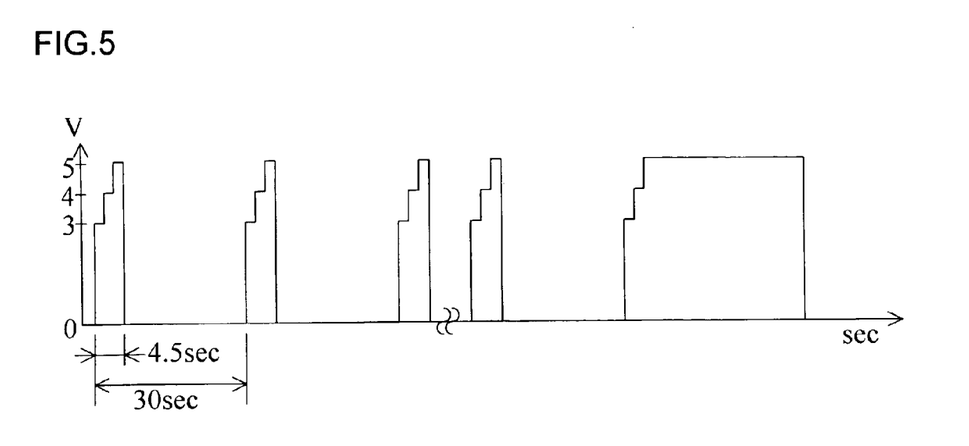
FIG. 5 is a graph for showing the ON/OFF control of the light source and the measurements according to Example 2.
Figure 6:
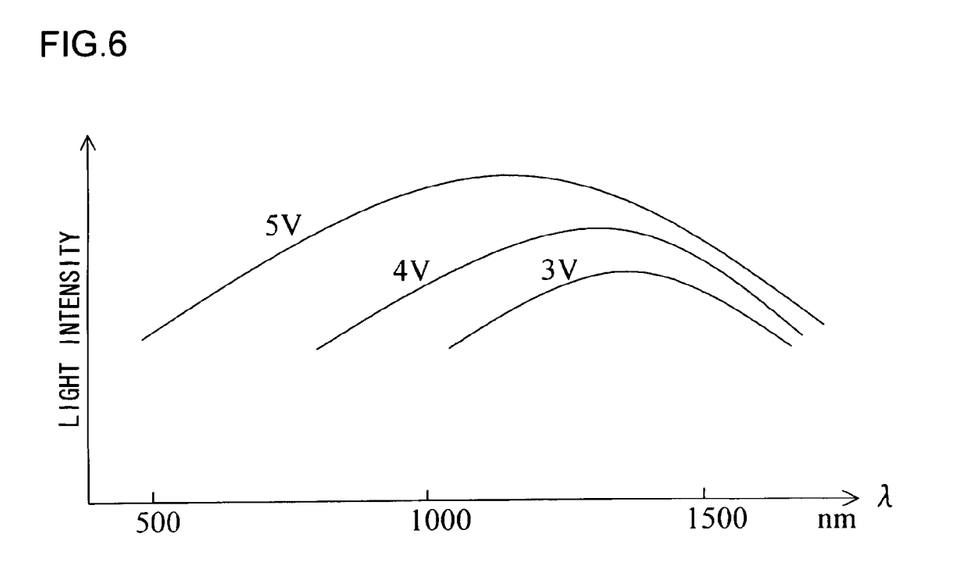
FIG. 6 is a schematic diagram showing the emission wavelength characteristics of an incandescent lamp.

In Example 2, as shown in FIG. 5, the light source 10 is lit with different voltages for 1.5 sec each, at intervals of 30 sec. When the light source 10 is an incandescent lamp, the voltage to be applied to the light source 10 can be changed to vary the waveband of the light to be emitted from the light source 10 as shown in FIG. 6. The light for the photoreceptors 18 and 20 to receive depends on the emission characteristics of the light source 10, the reflection characteristics of the mirror 12, the absorption characteristics of the aqueous solution, and the reception characteristics of the photoreceptors 18 and 20 themselves. Consequently, when the voltage to be applied to the light source 10 is changed in three steps to adjust the emission characteristics as shown in FIG. 5, it is possible to obtain a total of six types of signals from the two photoreceptors 18 and 20. This allows more accurate measurement of the concentration of the methanol aqueous solution. This also makes it easier to detect the presence of stains and contaminations from a combination of the signals of different wavebands.

Furthermore, when air bubbles or the like get mixed in as shown in FIG. 4, the light source 10 can be kept on, not turned off, so that the air bubbles expand due to the heat from the light source 10 as in Example 1. This makes it possible to reduce the energy consumption of the light source 10. Besides, even when air bubbles or the like hinder the measurement, it is possible to remove the air bubbles for proper measurement.

Reference Example

Figure 7:
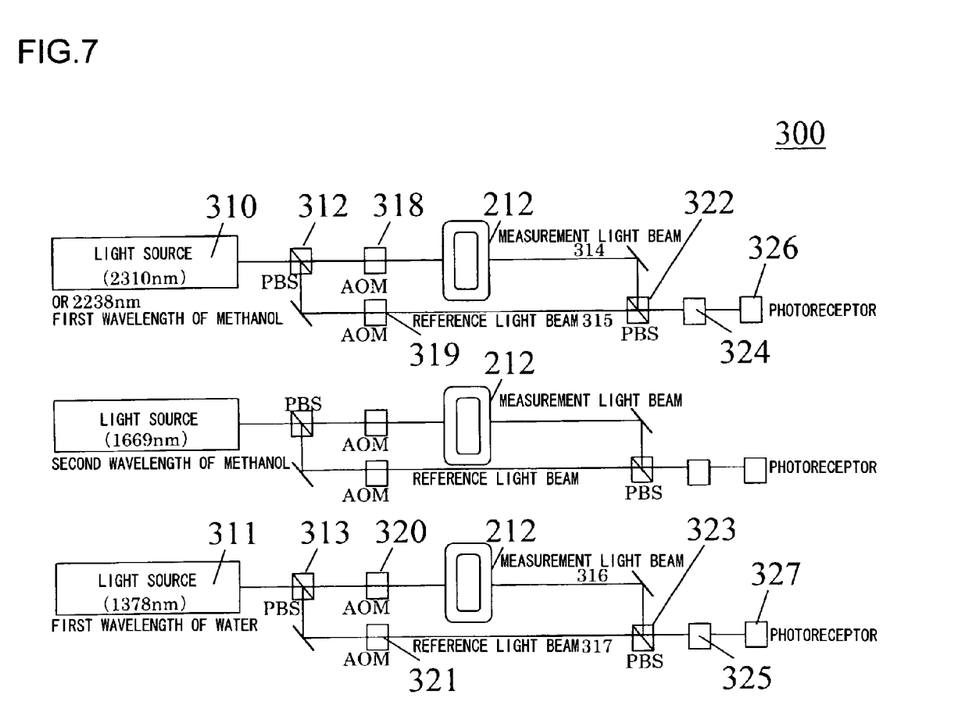
FIG. 7 is a schematic diagram showing the configuration of a concentration sensor according to a reference example.

FIG. 7 is a schematic diagram showing the configuration of a concentration sensor 300 according to a reference example. The concentration sensor 300 of this reference example may be installed in the same location as in the foregoing Examples.

Light sources for emitting coherent light (light sources for emitting laser light) are suited to the light sources of the concentration sensor 300 according to the reference example. Here, two types of light sources, or a first light source 310 having a wavelength of 2310 nm intended for methanol detection and a second light source 311 having a wavelength of 1378 nm intended for water detection, are used.

The light beams emitted from the light sources 310 and 311 are split by a first polarizing beam splitter 312 and a second polarizing beam splitter 313, respectively. The split light beams 314, 315, 316, and 317 are modified in light frequency by approximately 40 MHz (several tens of MHz to several hundreds of MHz or so) by using acousto-optic modulators (AOM) 318, 318, 320, and 321, respectively. The modification is such that the split light beams from each identical light source (the beam 314 and the beam 315, or the beam 316 and the beam 317) have slightly different frequencies.

Either ones of the split light beams, or measurement light beams 314 and 316, are projected onto the methanol aqueous solution supply pipe 212 so that their optical paths pass through the methanol aqueous solution. The others of the split light beams, or reference light beams 315 and 317, are passed through respective optical paths in the air, not through the methanol aqueous solution.

The measurement light beams 314 and 316 past the methanol aqueous solution are combined with the reference light beams from the respective identical light sources (i.e., the light beam 314 with the light beam 315, and the light beam 316 with the light beam 317) by a third polarizing beam splitter 322 and a fourth polarizing beam splitter 323, respectively. The resultants are passed through polarizing plates 324 and 325, respectively. Here, the light beams having slightly different frequencies are multiplied by each other, so that signals oscillating in light intensity at the frequency differences between the multiplied light beams are obtained from photoreceptors 326 and 327. This provides so-called optical heterodyne interferometers.

The optical heterodyne interferometers have the characteristics of having high noise immunity and being capable of high-precision high-sensitivity measurement since the signals can be amplified by the reference light beams even with a measurement system having the propensity to attenuate the measurement light beams. Consequently, it becomes possible to use the light sources of 2310 nm and 1378 nm, having significant light absorbabilities to methanol and water, for measurement. Besides, the wavelength with the significant light absorbabilities allow accurate concentration measurement. Furthermore, a third light source of 1669 nm, a reference wavelength intended for methanol detection, can be used to detect the concentration of the methanol aqueous solution more accurately.

Other Remarks

The foregoing embodiment has dealt with the case where the concentration sensor 100 is attached to the pipe immediately before the supply of the methanol aqueous solution to the anode of the DMFC. Nevertheless, the position of attachment is not limited to the pipe immediately before the supply of the methanol aqueous solution. The concentration sensor 100 may be attached to the buffer tank 232, a manifold area of the DMFC body 240, an exhausting pipe of the methanol aqueous solution, or the like. The dimensions of the pipe are desirably determined so that the optical length of the concentration sensor 100 will not exceed 5 mm. When the inner size of the pipe is equal to or exceeds 2.5 mm (or 5 mm in terms of the optical length) for the sake of securing a necessary flow rate, it is desirable that a subchannel of smaller thickness be provided and the concentration sensor 100 be arranged on that portion.

Figure 8:
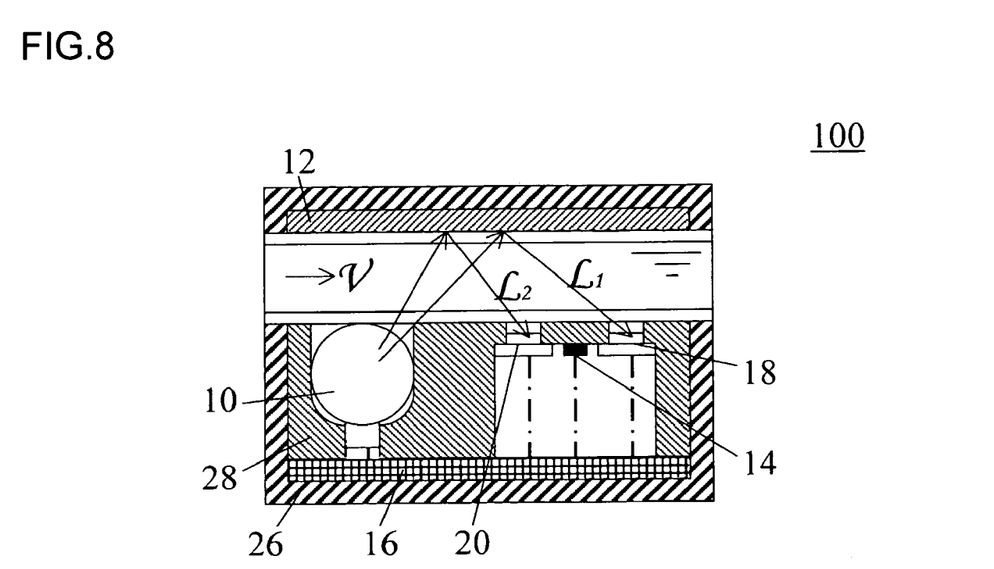
FIG. 8 is a schematic diagram showing the relationship between optical paths and the flow rate of the methanol aqueous solution.

As shown in FIG. 8, the light beams that have measured the same portion of the methanol aqueous solution seem to be incident on the photoreceptors with the first photoreceptor 18 later. This is ascribable to the relationship between the difference L between the optical length from the light source 10 to the first photoreceptor 18 and the optical length from the light source 10 to the second photoreceptor 20, and the velocity V of the methanol aqueous solution flowing through the methanol aqueous solution supply pipe 212. Then, the timing for the first photoreceptor 18 to measure the light beam can be corrected to come after that of the second photoreceptor 20. This correction allows even more accurate measurement.

The embodiment of the present invention has been described as specialized in DMFC. Nevertheless, the present invention which is capable of measuring the concentration of alcohols such as in the methanol aqueous solution with high precision may also be applied to manufacturing and testing processes of alcohol-containing beverages.

What is claimed is:

1. A fuel cell system comprising:
a fuel cell body having an anode to which a liquid fuel is supplied;
a mixing ratio detecting apparatus for detecting a mixing ratio of a component to be detected to a mixture solution containing the component to be detected and for detecting a mixing ratio of a fuel component to a liquid supplied to the fuel cell body, the apparatus comprising:
an incandescent light source which emits light including at least light of an infrared region;
a first light detecting unit which detects the light of the infrared region, the first light detecting unit being arranged in a position capable of receiving the light of the infrared region from the incandescent light source through the mixture solution;
a second light detecting unit which detects light of a region having a range different from that of the first light detecting unit, the second light detecting unit being arranged in a position capable of receiving the light from the light source through the mixture solution and at the distance from the incandescent light source smaller than the distance between the incandescent light source and the first light detecting unit; and
a control unit which outputs a signal pertaining to the mixing ratio based on signals from the first light detecting unit and the second light detecting unit, wherein
the control unit alternately turns on and off the incandescent light source so as to ensure that a period for which the light source is turned off is longer than a period for which the light source is turned on; and the control unit warms the liquid by maintaining the incandescent light source turned on when an abnormal signal is detected from the first light detecting unit or the second light detecting unit; the system further comprising:
a fuel unit which stores a fuel having a concentration higher than that of the liquid fuel to be supplied to the fuel cell body;
a liquid fuel supply unit which dilutes the high concentration fuel to supply the liquid fuel to the fuel cell body; and
a system control unit which controls the fuel cell system, and wherein
the system control unit issues an instruction to supply the high concentration fuel from the fuel unit to the liquid fuel supply unit in accordance with a signal from the mixing ratio detecting apparatus.

2. A fuel cell system comprising:
a fuel cell body having an anode to which a liquid fuel is supplied;
a mixing ratio detecting apparatus for detecting a mixing ratio of a component to be detected to a mixture solution containing the component to be detected and for detecting a mixing ratio of a fuel component to a liquid supplied to the fuel cell body, the apparatus comprising:
an incandescent light source which emits light including at least light of an infrared region;
a first light detecting unit which detects the light of the infrared region, the first light detecting unit being arranged in a position capable of receiving the light of the infrared region from the incandescent light source through the mixture solution;
a second light detecting unit which detects light of a region having a range different from that of the first light detecting unit, the second light detecting unit being arranged in a position capable of receiving the light from the light source through the mixture solution and at the distance from the incandescent light source smaller than the distance between the incandescent light source and the first light detecting unit; and
a control unit which outputs a signal pertaining to the mixing ratio based on signals from the first light detecting unit and the second light detecting unit, wherein
the control unit alternately turns on and off the incandescent light source,
wherein heat from the incandescent light source is adapted to be conducted to the mixture solution, and
the control unit warms the liquid by maintaining the incandescent light source turned on when an abnormal signal is detected from the first light detecting unit or the second light detecting unit;
the system further comprising:
a fuel unit which stores a fuel having a concentration higher than that of the liquid fuel to be supplied to the fuel cell body;
a liquid fuel supply unit which dilutes the high concentration fuel to supply the liquid fuel to the fuel cell body; and
a system control unit which controls the fuel cell system, and wherein
the system control unit issues an instruction to supply the high concentration fuel from the fuel unit to the liquid fuel supply unit in accordance with a signal from the mixing ratio detecting apparatus.

3. The fuel cell system according to claim 1, wherein
the system control unit receives a signal pertaining to a flow rate of the liquid fuel from the liquid fuel supply unit; and
the system control unit or the control unit of the mixing ratio detecting apparatus makes a flow rate correction to the signals obtained from the first light detecting unit and the second light detecting unit by using the signal pertaining to the flow rate received by the system control unit.

4. The fuel cell system according to claim 2, wherein
the system control unit receives a signal pertaining to a flow rate of the liquid fuel from the liquid fuel supply unit; and
the system control unit or the control unit of the mixing ratio detecting apparatus makes a flow rate correction to the signals obtained from the first light detecting unit and the second light detecting unit by using the signal pertaining to the flow rate received by the system control unit.

5. The fuel cell system according to claim 1, wherein the liquid fuel is a methanol aqueous solution.

6. The fuel cell system according to claim 2, wherein the liquid fuel is a methanol aqueous solution.

7. The fuel cell system according to claim 3, wherein the liquid fuel is a methanol aqueous solution.

8. The fuel cell system according to claim 4, wherein the liquid fuel is a methanol aqueous solution.

9. The fuel cell system according to claim 2, wherein at least one major surface of the mixing ratio detecting apparatus is covered with a heat insulating member.

10. The fuel cell system according to claim 9, wherein
the system control unit receives a signal pertaining to a flow rate of the liquid fuel from the liquid fuel supply unit; and
the system control unit or the control unit of the mixing ratio detecting apparatus makes a flow rate correction to the signals obtained from the first light detecting unit and the second light detecting unit by using the signal pertaining to the flow rate received by the system control unit.

11. The fuel cell system according to claim 9, wherein the liquid fuel is a methanol aqueous solution.

12. The fuel cell system according to claim 10, wherein the liquid fuel is a methanol aqueous solution.

* * * * *